United States Patent
Jago et al.

(10) Patent No.: US 10,070,846 B2
(45) Date of Patent: *Sep. 11, 2018

(54) ULTRASONIC VOLUME FLOW MEASUREMENT FOR ABLATION THERAPY

(71) Applicant: KONINKLIJKE PHILIPS N.V., Eindhoven (NL)

(72) Inventors: James Robertson Jago, Eindhoven (NL); Gary Cheng-How Ng, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 291 days.

This patent is subject to a terminal disclaimer.

(21) Appl. No.: 14/424,509

(22) PCT Filed: Aug. 12, 2013

(86) PCT No.: PCT/IB2013/056585
§ 371 (c)(1),
(2) Date: Feb. 27, 2015

(87) PCT Pub. No.: WO2014/033577
PCT Pub. Date: Mar. 6, 2014

(65) Prior Publication Data
US 2015/0223779 A1 Aug. 13, 2015

Related U.S. Application Data

(60) Provisional application No. 61/696,156, filed on Sep. 1, 2012.

(51) Int. Cl.
*A61B 8/00* (2006.01)
*A61B 8/06* (2006.01)
(Continued)

(52) U.S. Cl.
CPC .............. *A61B 8/469* (2013.01); *A61B 8/06* (2013.01); *A61B 8/0891* (2013.01); *A61B 8/483* (2013.01);
(Continued)

(58) Field of Classification Search
CPC .................................. A61B 8/06; A61B 34/10
See application file for complete search history.

(56) References Cited

U.S. PATENT DOCUMENTS

| 5,474,073 A | 12/1995 | Schwartz et al. |
| 5,720,291 A | 2/1998 | Schwartz |

(Continued)

FOREIGN PATENT DOCUMENTS

| CN | 102232857 A | 11/2011 | |
| WO | WO 2011080666 A1 * | 7/2011 | ............. A61B 18/12 |

(Continued)

OTHER PUBLICATIONS

"Radio Frequency Ablation of Liver Turmors: Actual Limitations and Potential Solutions in the Future" Kunzli et a, World J. Hepatol Jan. 27, 2011 p. 8-14.

(Continued)

*Primary Examiner* — Rajeev Siripurapu (57) ABSTRACT

A method for ablation treatment using ultrasound data begins by identifying pathology to be treated and one or more blood vessels proximate the treatment site in a medical diagnostic image. The identified ROI and the blood vessels are automatically indicated in an ultrasound image Ultrasonic Doppler velocity data is acquired from the flow within the vessels and the Doppler data is used to calculate the volume blood flow through the vessels. The thermal effect of the heat transported by this blood flow is considered in the (Continued)

planning or conduct of the ablation treatment, as by modifying the size of a burn zone graphic around the tip of the ablation probe.

12 Claims, 4 Drawing Sheets

(51) Int. Cl.
*A61B 8/08* (2006.01)
*A61B 8/14* (2006.01)
*A61B 18/00* (2006.01)
*A61B 90/00* (2016.01)
*A61B 34/10* (2016.01)

(52) U.S. Cl.
CPC ............... *A61B 8/488* (2013.01); *A61B 8/14* (2013.01); *A61B 8/5261* (2013.01); *A61B 18/00* (2013.01); *A61B 2018/00529* (2013.01); *A61B 2018/00577* (2013.01); *A61B 2034/105* (2016.02); *A61B 2090/364* (2016.02)

(56) References Cited

U.S. PATENT DOCUMENTS

| | | |
|---|---|---|
| 5,997,479 A | 12/1999 | Savord |
| 6,013,032 A | 1/2000 | Savord |
| 6,306,096 B1 | 10/2001 | Seward et al. |
| 6,368,281 B1 | 4/2002 | Solomon |
| 6,419,633 B1 | 7/2002 | Robinson et al. |
| 6,443,896 B1 | 9/2002 | Detmer |
| 6,491,636 B2 | 12/2002 | Chenal et al. |
| 6,663,568 B1 | 12/2003 | Gill |
| 6,709,394 B2 | 3/2004 | Frisa et al. |
| 6,780,155 B2 | 8/2004 | Li et al. |
| 2007/0161897 A1 | 7/2007 | Sasaki et al. |
| 2009/0177089 A1 | 7/2009 | Govari et al. |
| 2011/0015628 A1 | 1/2011 | Dalal et al. |
| 2011/0092880 A1 | 4/2011 | Gertner |
| 2011/0208055 A1* | 8/2011 | Dalal et al. ............... A61N 7/02 600/439 |
| 2012/0010479 A1 | 1/2012 | Eusemann |
| 2012/0065492 A1 | 3/2012 | Gertner et al. |
| 2013/0226003 A1* | 8/2013 | Edic ....................... A61B 5/026 600/454 |
| 2015/0209115 A1 | 7/2015 | Jago et al. |

FOREIGN PATENT DOCUMENTS

| | | |
|---|---|---|
| WO | 2011145020 A1 | 11/2011 |
| WO | 2014033600 A1 | 3/2014 |

OTHER PUBLICATIONS

"Radiofreqnecy Ablation of Procine Liver In Vivo" Patterson et al, Annals of Surgery, Vol. 227, No. 4, p. 559-565.

* cited by examiner

ULTRASONIC VOLUME FLOW MEASUREMENT FOR ABLATION THERAPY

This application is the U.S. National Phase application under 35 U.S.C. § 371 of International Application No. PCT/IB2013/056585, filed on Aug. 12, 2013, which claims the benefit of U.S. Provisional Application No. 61/696,156 filed on Sep. 1, 2012. These applications are hereby incorporated by reference herein.

This invention relates to medical diagnostic ultrasound systems and, in particular, to diagnostic ultrasound systems which provide a measure of blood volume flow for ablation therapy.

The use of local and minimally invasive therapies as alternatives to surgery are growing rapidly for the treatment of many lesions, especially cancer, and in many parts of the body. The advantages of these minimally invasive treatments include fewer side effects, faster recovery and, in some cases, the possibility to treat more advanced disease. One of the most important of these minimally invasive therapies is tissue ablation, where the diseased tissue is destroyed by application of local tissue heating, cooling, or other means. Some examples of ablation methods in most common use are r.f ablation, microwave ablation, HIFU (high intensity focused ultrasound), and cryo-ablation.

One of the key steps for successful tissue ablation is to determine, prior to conducting the procedure, the appropriate placement of the ablation probe within the lesion and the duration of treatment. Each ablation probe has a treatment region around which the temperature is changed enough to cause cell death. This region is typically called the "burn zone". Fully covering the cancerous lesion with the burn zone ensures that there are no residual cells that could result in recurrence of the cancer. This treatment planning involves assessing the size and shape of the target lesion, typically with CT images and, using known information about the available intensity levels of the ablation device, calculating a predicted treatment volume based on selected treatment times and/or the number of separate ablations required to treat the entire lesion. Specifications for the ablation region associated with a given ablation method, needle size, treatment intensity and time, etc., are provided by manufacturers of ablation devices and are typically based on characterization of those devices performed by their respective manufacturers in a controlled, static environment without the presence of actively circulating blood vessels.

One challenge for treatment planning is in situations where the target lesion is close to a blood vessel or vessels, which can occur frequently in, for example, liver ablations. It is common in planning a treatment procedure to identify the location of nearby vessels so that they are not damaged in the conduct of the treatment of the lesion. Damaging or disabling blood vessels which supply blood to healthy organs and tissue is to be avoided. One problem which has not been fully addressed heretofore is that the blood flowing through a nearby vessel can have a significant cooling or warming effect (i.e., as a heat sink which conveys thermal treatment energy away from the treatment site) on the tissue, which causes the actual treatment volume to be different from the volume specified by the device manufacturer and used in the treatment plan, and which can ultimately lead to incomplete ablation of the lesion and risk of recurrence of disease. For example, Patterson et al (1998) demonstrated experimentally in porcine liver in vivo that the presence of blood vessels can alter the diameter of an r.f. ablation treatment volume by up to 200%. In an attempt to compensate for the cooling effect of vessels, some imaging companies provide treatment planning applications that allow the larger vessels to be identified in the image data, for example from contrast CT images, and then the treatment plan can be adjusted. However, since contrast CT images only show where the vessels are located and not how much blood is flowing through them, it is not possible to accurately predict the cooling effect and hence the treatment plan may still be incorrect.

Cancerous and other benign lesions are especially dangerous due to their rampant growth in the body, rapidly spreading their disease conditions and adversely affecting and crowding healthy organs and tissue. To fuel this rampant growth, these lesions develop their own vasculature which diverts the body's flow of nourishing blood to these lesions. The flow of blood into and out of a cancerous region can also be a contributor to diminishing the thermal effect of ablation energy delivery.

In order to predict how blood flow in nearby vessels affects the ablation region, one must create a model that characterizes this effect. This model may be developed experimentally, for example using animal models either in-vivo or ex-vivo, or it may be developed from theoretical principles. For example, modifications to the bioheat equations have been developed that incorporate vessels and flow, although solutions to these typically require finite element methods. The problem for existing methods is that, in order for these models to be reasonably accurate, knowledge of the amount of blood volume (e.g., ml/min) flowing through the vessels is required, and this information is currently not readily available using any non-invasive technique. Accordingly, it is desirable to be able to non-invasively measure blood flow volumes and quantify the thermal effect of regional blood flow and take this information into consideration when planning an ablation procedure.

In accordance with the principles of the present invention, diagnostic imaging is conducted prior to an ablation procedure to identify blood vessels that are in close proximity to a lesion to be treated with ablative therapy. The diagnostic imaging modality can be CT, MR, ultrasound or any other modality capable of visualizing blood vessels. A diagnostic ultrasound system is then used at the time of the procedure to obtain 3D ultrasound Doppler data from the identified blood vessels. The amount of blood flowing through the identified blood vessels is calculated from the Doppler data such as by integrating the flow velocity over the area of a vessel lumen. The amount of blood flow thus measured is used to develop or modify an ablation treatment plan that takes the thermal effects of this blood flow into consideration. The blood flow information can be used, for example, to modify the predicted r.f. ablation treatment volume for manual planning, or included as input to an automated treatment planning algorithm that seeks to maximize treatment efficacy.

In accordance with another implementation of the present invention, the ultrasound transducer has tracking capability, for example using electromagnetic (EM) tracking as provided by the Philips Percunav® system. The reference frame of the ultrasound system is aligned with the corresponding image of the imaging modality used to identify the vessels of interest (e.g., through plane matching or automated methods provided by the image fusion capability of the Percunav system) and, since the transducer location is also known, the Doppler region of interest is placed automatically on the vessels of interest, thus improving accuracy, efficiency and ease of use.

Figure 1:
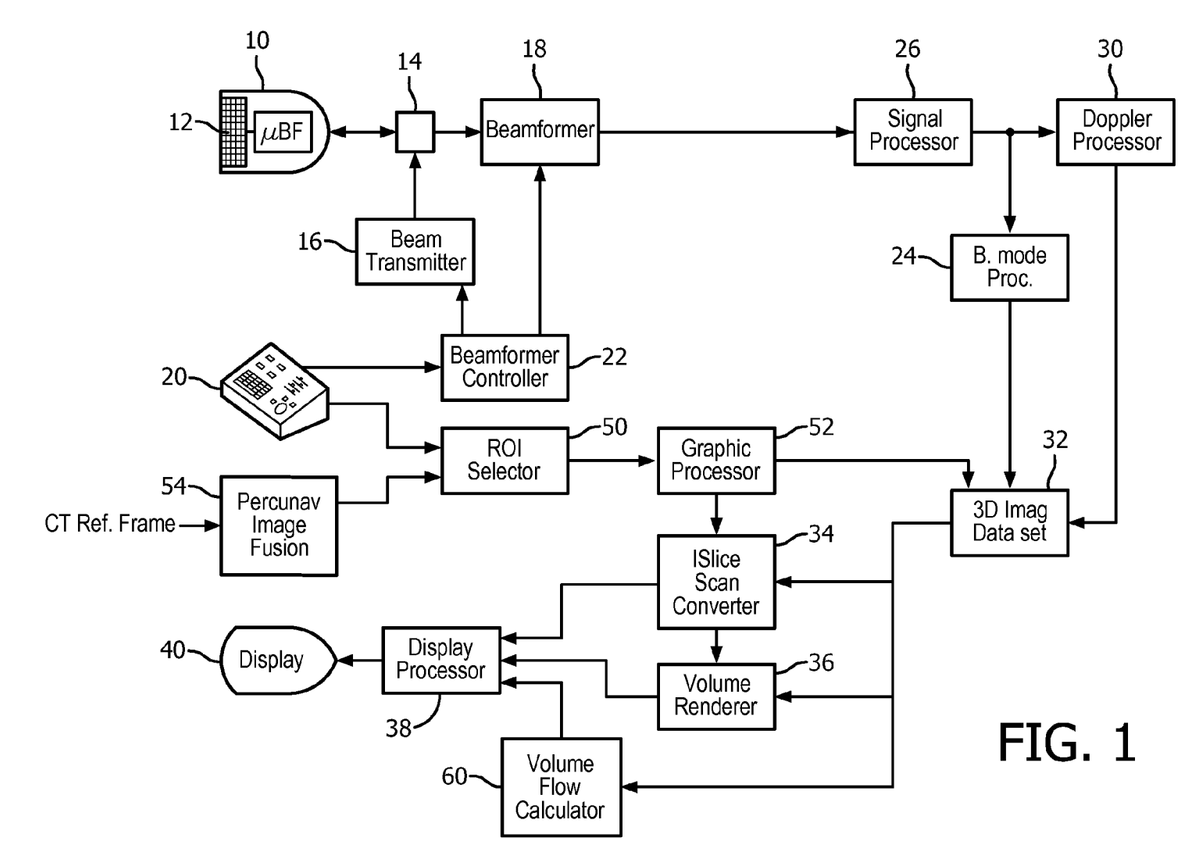
FIG. 1 illustrates an ultrasonic diagnostic imaging system constructed to operate in accordance with the principles of the present invention.

Referring first to FIG. 1, an ultrasonic diagnostic imaging system constructed in accordance with the principles of the present invention is shown in block diagram form. An ultrasound probe 10 capable of three dimensional imaging includes a two dimensional array transducer 12 which transmits electronically steered and focused beams over a volumetric region and receives single or multiple receive beams in response to each transmit beam. Groups of adjacent transducer elements referred to as "patches" or "subarrays" are integrally operated by a microbeamformer (μBF) in the probe 12, which performs partial beamforming of received echo signals and thereby reduces the number of conductors in the cable between the probe and the main system. Suitable two dimensional arrays are described in U.S. Pat. No. 6,419,633 (Robinson et al.) and in U.S. Pat. No. 6,368,281 (Solomon et al.) Microbeamformers are described in U.S. Pat. No. 5,997,479 (Savord et al.) and U.S. Pat. No. 6,013,032 (Savord). The transmit beam characteristics of the array are controlled by a beam transmitter 16, which causes the apodized aperture elements of the array to emit a focused beam of the desired breadth in a desired direction through a volumetric region of the body. Transmit pulses are coupled from the beam transmitter 16 to the elements of the array by means of a transmit/receive switch 14. The echo signals received by the array elements and microbeamformer in response to a transmit beam are coupled to a system beamformer 18, where the partially beamformed echo signals from the microbeamformer are processed to form fully beamformed single or multiple receive beams in response to a transmit beam. A suitable beamformer for this purpose is described in the aforementioned Savord '032 patent.

The receive beams formed by the beamformer 18 are coupled to a signal processor 26 which performs functions such as filtering and quadrature demodulation. The echo signals of the processed receive beams are coupled to a Doppler processor 30 and a B mode processor 24. The Doppler processor 30 processes the echo information into spatially resolved Doppler power or velocity information. For B mode imaging the receive beam echoes are envelope detected and the signals logarithmically compressed to a suitable dynamic range by the B mode processor 24. The echo signals from the volumetric region are buffered in the form of a 3D image dataset 32. The 3D image data may be processed for display in several ways. One way is to produce one or more 2D planes of the volume. This is described in U.S. Pat. No. 6,443,896 (Detmer). Such planar images are formed by addressing data of the 3D image data set in spatially discrete image planes, known as multi-planar reformatting. The three dimensional image data may also be rendered to form a perspective or kinetic parallax 3D display by a volume renderer 36. A third way is to produce an "iSlice" image, which is formed by iSlice scan converter 34 from image data of a repetitively scanned plane of the 3D volume. By only scanning one or a few image planes in the volume, the scanning can be done rapidly enough to produce one or more live 2D iSlice images. An effective use of iSlice imaging is performed in what is known as biplane imaging, in which two or more iSlice images are concurrently displayed and can be spatially manipulated with respect to each other as described in U.S. Pat. No. 6,709,394 (Frisa et al.) One preferred biplane mode is the rotate mode, in which one iSlice image has a fixed orientation with respect to the probe 10 and a second iSlice image intersects the first at a common central scanline and can be rotated around that scanline. The first image provide a spatial reference for the user, and the second image can be rotated to view intersecting planes in the volume. Biplane imaging is useful in the practice of the present invention as described below. The resulting 2D or 3D images, which may be B mode, Doppler or both as described in U.S. Pat. No. 5,720,291 (Schwartz), are coupled to a display processor 38, from which they are displayed on an image display 40. In accordance with the present invention, a volume flow calculator 60 is coupled to receive selected Doppler flow data from the 3D image data set 32. The volume flow calculator calculates volume flow of blood in ml/sec., preferably by integration of the flow data of a surface that intersects a blood vessel as described in U.S. Pat. No. 6,780,155 (Li et al.) or U.S. Pat. No. 6,663,568 (Gil). The volume flow calculation is coupled to the display processor 38 for display on the display 40. User control of the beamformer controller 22 and other functions of the ultrasound system are provided through a user interface or control panel 20.

Figure 2:
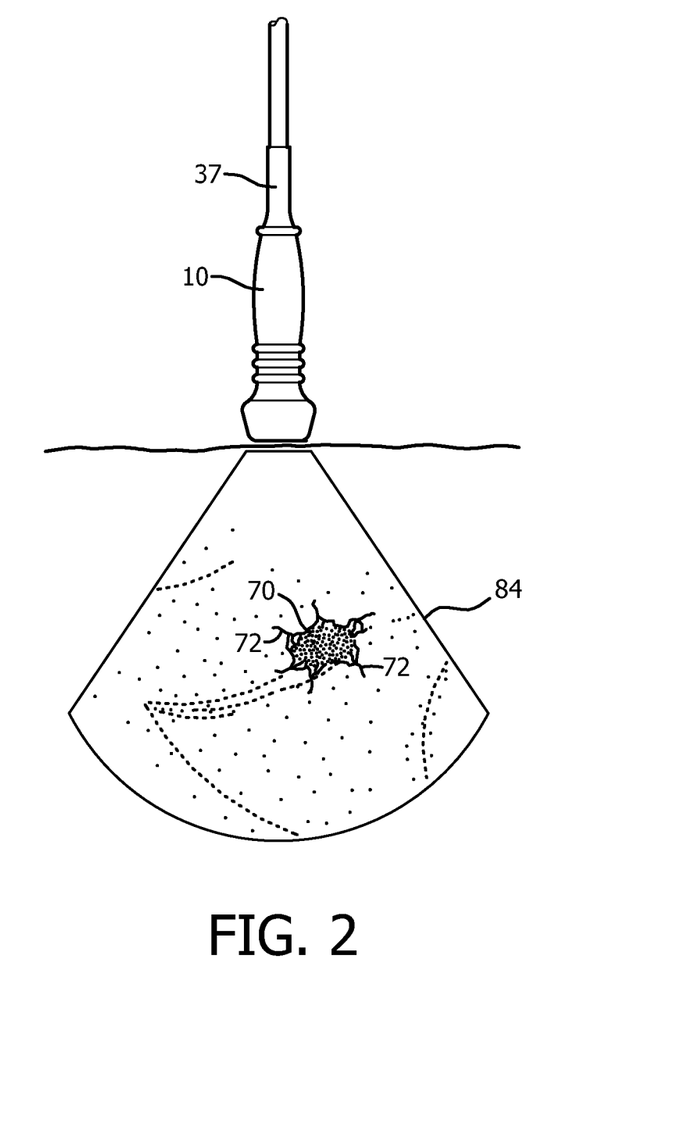
FIG. 2 illustrates the ultrasonic imaging of a lesion to be ablated and its vasculature using the ultrasound probe shown in FIG. 1.
Figure 3:
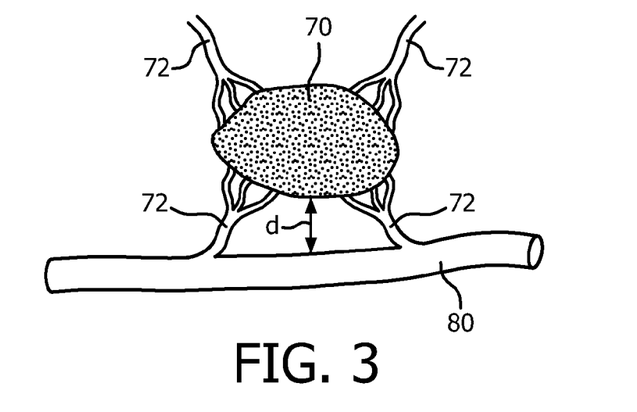
FIG. 3 is an enlarged view of the lesion of FIG. 2 and its vasculature.

FIG. 2 shows ultrasound probe 10 imaging an iSlice image plane 84 of a region of the body such as the liver. In this example the probe 10 is connected to the ultrasound system by a cable and strain relief 37. The iSlice image displays pathology to be treated by ablation, in this case a lesion 70 in the liver such as an HCC lesion. The lesion 70 is seen to be supplied with blood from a surrounding network of vasculature 72. FIG. 3 is an enlarged view of the lesion 70 and its vasculature, in this view revealing the presence of a nearby large blood vessel 80. In this example the blood vessel 80 is seen to be a source of blood supply for some of the blood vessels of the vasculature 72, although this is not always the situation in a given patient; the large blood vessel 80 may simply be passing through the tissue near the lesion 70. The blood vessel 80 is seen to have its closest proximity to the lesion 70 at a point where it is a distance "d" from the lesion.

Figure 4A:
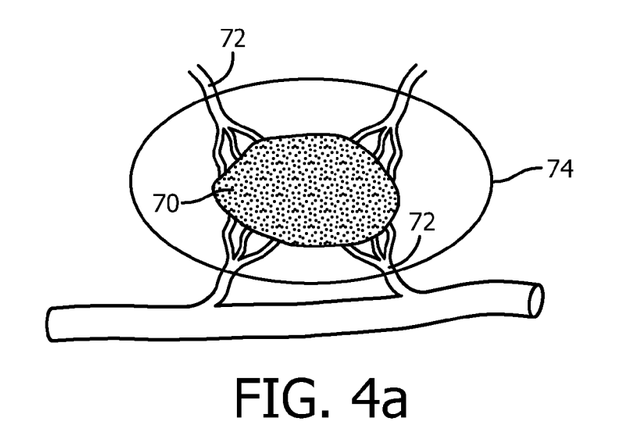
FIGS. 4a and 4b illustrate the segmentation of the volumetric region of a lesion and its supply vasculature for blood volume flow measurement in accordance with the principles of the present invention.

FIGS. 4a and 4b illustrate one implementation of the present invention in which the thermal transfer effect of the blood flow to and from the lesion 70 is determined. In a case where the vasculature nourishing the lesion includes a number of well defined major vessels as illustrated by blood vessels 72 in FIG. 3, the volume flow of these vessels can be identified and calculated. FIG. 4a illustrates an ultrasound image of the lesion and its vasculature around which a user has placed an enclosing shape 74. In this example the shape 74 is an oval shape which is seen to intersect the major vessels of the blood supply vessels 72. The user can use the control panel 20 to select a shape of a desired size and shape from an ROI (region of interest) selector 50. The shape is manipulated on the screen from the control panel until it is properly placed to intersect the major vessels as shown in FIG. 4a. The shape 74 in this example is an oval in two dimensions and an ellipsoid in three dimensions. The biplane imaging mode is well suited to manipulate the shape 70 around the lesion 70, since the user can view initial placement of the shape 74 in one plane as shown in FIG. 4a, then view the shape as the other biplane image is rotated about the center of the first image, observing that the shape fully encloses the lesion and intersects its supply vessels. While the present example shows an oval or ellipsoidal shape, other shapes such as a circle, sphere, square or rectangular box, or square cubic or rectangular cubic shape can also be used.

Alternatively, the shape or a graphic designating the ROI is placed automatically in the ultrasound image by the system if the ultrasound image has been aligned (e.g. by multi-modality image registration) with the reference frame of a pre-procedure planning modality. A standard practice in planning an ablation procedure is to first image the pathology by CT or MR imaging. An image in this modality is then analyzed to identify the lesion and its feeding or neighboring blood vessels by a vessel segmentation algorithm. A system which performs this analysis is the Extended Brilliance CT workstation available from Philips Healthcare of Andover Mass. This workstation has a CT vessel segmentation algorithm which will automatically mark blood vessels to be quantified on a CT image, which then becomes the CT reference image frame for the procedure. When the patient is thereafter scanned with 3D ultrasound, a multi-modality image registration system such as an ultrasound system equipped with the Percunav® image fusion option 54 can register the CT reference image with an anatomically matching ultrasound image from the ultrasound 3D dataset. Once aligned, the delineation of the blood vessels marked on the CT image is translated to the ultrasound image, automatically identifying the ROI and/or the vessels to be quantified by ultrasound in the ultrasound image.

Figure 4B:
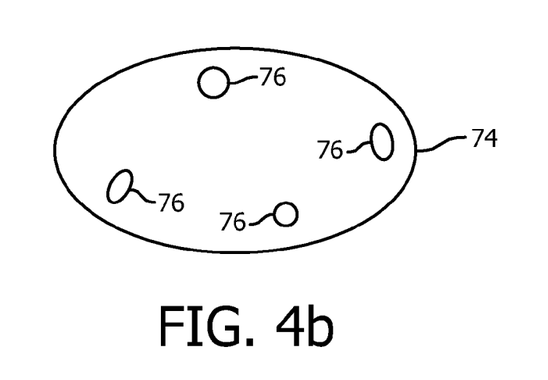

The surface of the enclosing shape 74 intersects the blood vessels passing through it as illustrated in FIG. 4b. Cross-sectional surfaces 76 of the blood vessels are delineated by the shape 74. The Doppler flow of blood vessels when separately presented from its surrounding B mode tissue image segments the flow of blood in the vessels as explained in U.S. Pat. No. 5,474,073 (Schwartz et al.) The volume flow of each vessel 72 can be calculated by integration of the Doppler flow values of the flow surfaces 76 that intersects surrounding surface 74. The direction of the blood flow is integrated by the relative polarity of the Doppler signals, identifying the flow of fresh (unablated) blood into the lesion 70 and the flow of thermally treated blood away from the lesion. By summing the different flow volumes the total volume flow to and from the lesion can be calculated and the net effect on thermal transfer estimated. The effect of this thermal transfer can then be used to plan the ablation treatment.

Figure 5A:
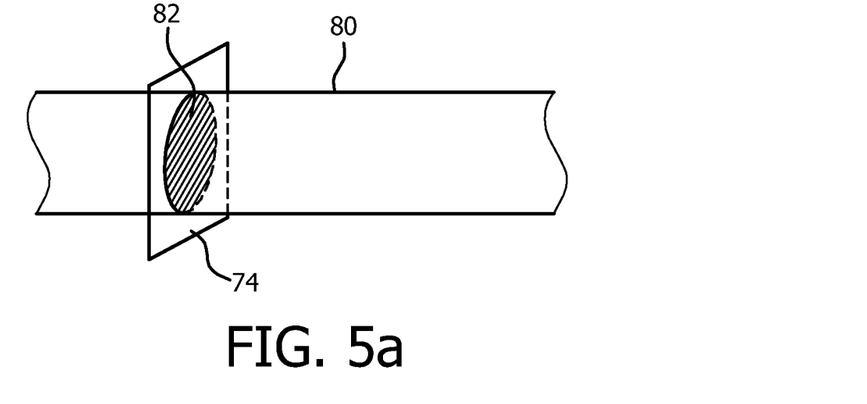
FIGS. 5a and 5b illustrate the measurement of blood volume flow of a blood vessel proximate a lesion to be treated by ablation in accordance with the principles of the present invention.
Figure 5B:
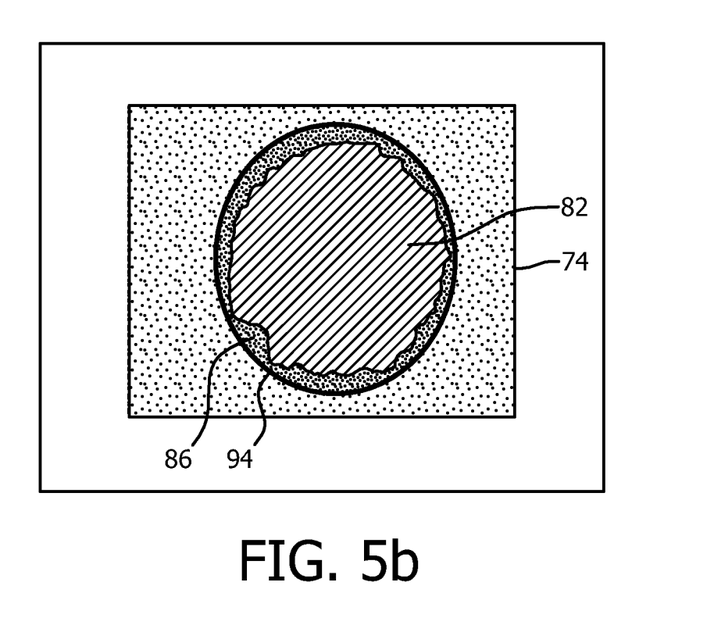

In some cases it may be desirable to additionally consider the thermal transfer effect of the blood flow in the large neighboring vessel 80. In other cases the large neighboring vessel may be seen as the dominant factor in thermal transfer and only the volume flow of the large vessel is calculated and considered in ablation treatment planning. For a large vessel like blood vessel 80 of FIG. 3, surface shape 74 used to delineate the flow of the vessel can be a single plane as illustrated in FIG. 5a. The shape 74 is positioned to intersect the flow 82 of the vessel 80 at an orthogonal or other angle as explained in the Li et al. and Gill patents. This intersection will effectively project the Doppler flow 82 of the vessel 80 onto the plane of the shape 74 as illustrated in FIG. 5b. In this example an optional template 94 has been placed around the flow area 82 and the endothelial wall 86 of the lumen of blood vessel 80. The blood flow velocity of the Doppler data values of the flow surface 82 is integrated over the flow area to calculate the volume flow rate through the vessel 80 in ml/min. The volume flow of the vessel 80 is shown on the screen of display 40 where it can be accessed and used in conjunction with the proximity of the vessel to the treatment site (distance "d" in FIG. 3) and the thermal transport properties of the intervening tissue to plan the ablation therapy of lesion 70.

A typical ablation planning process may proceed as follows. Planning may be done for a liver r.f. ablation procedure, where an HCC lesion has been previously identified on a contrast CT scan. The clinician would first review this CT study in order to develop a preliminary treatment plan (e.g., deciding on the ablation needle tip location and the nominal r.f. intensity and duration). The clinician may also execute a CT segmentation algorithm, such as one which is commercially available on CT image analysis workstations, that highlights the blood vessels within the liver. Upon identifying a large vessel that is close to the target lesion, the clinician would then understand that this vessel could have a significant effect on the treatment plan. At the beginning of the procedure, the clinician starts scanning with an ultrasound system, the co-ordinates of which had already been registered to the CT co-ordinate system. Various methods exist for registering medical diagnostic images, including external fiducial-based methods and manual tissue landmark-based methods. The Percunav® image fusion option available on the iU22 ultrasound system from Philips Healthcare of Andover, Mass. is capable of anatomically registering CT and ultrasound images. By viewing the ultrasound image superimposed on the CT image, including the segmentation of the vessels from the CT data, the clinician would be easily able to target a 3D Doppler ultrasound volume acquisition through the vessel that is close to the target lesion. The identification of the 3D Doppler ultrasound volume in the aligned images may also be automated as described previously, based on the treatment plan. An algorithm would then calculate the blood volume flowing through this vessel, and this information would then be used to modify the treatment plan and hence adjust the needle placement, r.f. intensity and/or duration. A previously acquired CT, MR or 3D ultrasound volume or 3D contrast ultrasound volume may be used as the reference image input to a treatment plan, and for identifying blood vessels near the target lesion.

Other approaches may also be taken. For instance, it may be of benefit to divide the treatment into multiple phases of treatment, since the blood flow may itself change in response to the treatment. The clinician could perform an initial phase of the planned treatment, taking into consideration the thermal transfer effects of both the supply vessels to the lesion and that of a nearby large blood vessel. The initial phase of treatment may debilitate the lesion such that the blood flow of the supply vessels is largely eliminated. The blood flow of the nearby large vessel is then re-measured and its thermal transport effect re-evaluated to re-calculate the remaining treatment required to complete the ablation procedure.

Other variations of the present invention may also be employed. For instance, ultrasonic automated border detection may be used to identify and delineate the size of blood vessel lumens as described in U.S. Pat. No. 6,491,436 (Chenal et al.) The volume flow of the traced blood vessel lumens is then calculated from their size and Doppler flow data. In a particular implementation of the present invention the flow-delineating shapes and surfaces may be displayed or not displayed at the choice of the system designer.

A system of the present invention can be used in procedures even in cases where pre-procedure treatment planning is not used. For instance, the lesion and the blood vessels near the lesion are identified with live ultrasound. The ablation probe is introduced into the body and guided into the lesion. The Percunav® EM tracking system, by tracking the location of the probe, provides the ability to display the treatment region (or burn zone) as a graphical overlay around the tip of the ablation probe. The ablation device manufacturer's specified burn zone is used as the initial definition of the burn zone, providing the starting shape and size of the burn zone graphic around the probe tip. Once the flow data from the nearby vessels is measured by Doppler ultrasound in accordance with the present invention, the thermal effect of the flow is used to adjust the burn zone overlay around the probe. The system may initially show a relatively large burn zone around the probe tip, for instance, which is then modified to show a smaller burn zone once the thermal effect of the nearby blood flow is weighed. The user can then adjust the treatment time or other procedure parameters to fully ablate the target lesion.

What is claimed is:

1. A method for using ultrasonic information for ablation treatment of pathology comprising:
    receiving, at a processor of an ultrasonic imaging system, a treatment planning image of pathology to be treated by ablation and a plurality of blood vessels, the plurality of blood vessels comprising one or more blood vessels supplying blood flow to the pathology and one or more blood vessels carrying away blood flow from the pathology;
    controlling, by the processor, an ultrasound probe in communication with the ultrasonic imaging system to obtain an ultrasound image representative of the plurality of blood vessels;
    identifying, by the processor, the pathology to be treated by ablation in the ultrasound image;
    identifying, by the processor, the plurality of blood vessels in the ultrasound image, wherein the identifying includes placing a surface shape at a region of interest in the ultrasound image, the surface shape intersecting the plurality of blood vessels in the ultrasound image;
    receiving, at the processor, three dimensional ultrasound Doppler data acquired by the ultrasound probe and representative of the blood flow of the plurality of blood vessels intersecting the surface shape;
    calculating, by the processor, an amount of blood flowing through the plurality of blood vessels using the ultrasound Doppler data; and
    determining a heat transport characteristic of the amount of blood flowing through the plurality of blood vessels such that a parameter of an ablation device for treating the pathology is controlled based on at least the heat transport characteristic, wherein the determining is based on untreated blood flow into the pathology and thermally treated blood flow away from the pathology, wherein the placing the surface shape is performed automatically using knowledge of a location of the blood vessels obtained by registration of the ultrasound image with the treatment planning image.

2. The method of claim 1, wherein receiving three dimensional ultrasound Doppler data further comprises acquiring three dimensional ultrasound Doppler velocity data from the blood flow of an identified vessel.

3. The method of claim 2, wherein calculating the amount of blood flowing through an identified blood vessel further comprises delineating a surface through the blood flow of a vessel and integrating flow velocity data over an area of the surface.

4. The method of claim 1, wherein identifying the plurality of blood vessels further comprises identifying the plurality of blood vessels in a three dimensional ultrasound image.

5. The method of claim 1, wherein identifying the plurality of blood vessels further comprises identifying the plurality of blood vessels in two dimensional biplane ultrasound images.

6. The method of claim 1, wherein receiving the treatment planning image further comprises acquiring a CT image of pathology and a structure of the plurality of blood vessels; wherein placing the surface shape automatically comprises anatomically registering an ultrasound reference image with the CT image.

7. The method of claim 1, wherein placing the surface shape comprises placing a three dimensional shape at the region of interest in the ultrasound image such that the three dimensional shape intersects with the plurality of blood vessels in the ultrasound image.

8. The method of claim 1, wherein placing the surface shape comprises placing a two dimensional shape at the region of interest in the ultrasound image such that the two dimensional shape intersects with the plurality of blood vessels in the ultrasound image.

9. The method of claim 1, further comprising developing an ablation treatment plan based on the heat transport characteristic, volume blood flow of a vessel of the plurality of blood vessels, and a proximity of the vessel of the plurality of blood vessels to the identified pathology.

10. A system for using ultrasonic information for ablation treatment of pathology, the system comprising:
    an ultrasound probe; and
    a processor in communication with the ultrasound probe and an ablation device, the processor operable to:
        control the ultrasound probe to obtain an ultrasound image representative of a plurality of blood vessels, the plurality of blood vessels comprising one or more blood vessels supplying blood flow to the pathology and one or more blood vessels carrying away blood flow from the pathology;
        identify a pathology to be treated by ablation in the ultrasound image;
        identify the plurality of blood vessels in the ultrasound image, wherein the identifying includes placing a surface shape at a region of interest in the ultrasound image, the surface shape intersecting the plurality of blood vessels in the ultrasound image;
        receive three dimensional ultrasound Doppler data acquired by the ultrasound probe and representative of the blood flow of the plurality of blood vessels intersecting the surface shape;
        calculate an amount of blood flowing through the plurality of blood vessels using the ultrasound Doppler data; and
        use a heat transport characteristic of the amount of blood flowing through the plurality of blood vessels to control a graphical display of a treatment region of the ablation device and to control a parameter of the ablation device for treating the pathology, wherein the heat transport characteristic is based on untreated blood flow into the pathology and thermally treated blood flow away from the pathology.

11. The system of claim 10, wherein the processor is configured to identify pathology to be treated by ablation in a non-ultrasound diagnostic image, and anatomically register the non-ultrasound diagnostic image with an ultrasound image.

12. The system of claim 10, wherein the ablation treatment further comprises r.f ablation, microwave ablation, HIFU, or cryo-ablation therapy.

* * * * *